United States Patent [19]

Bohl

[11] Patent Number: 4,562,044

[45] Date of Patent: Dec. 31, 1985

[54] ON-LINE COAL ANALYZER

[75] Inventor: Thomas L. Bohl, Madison, Ohio

[73] Assignee: The Babcock & Wilcox Company, New Orleans, La.

[21] Appl. No.: 644,653

[22] Filed: Aug. 27, 1984

Related U.S. Application Data

[63] Continuation of Ser. No. 395,427, Jul. 6, 1982, abandoned.

[51] Int. Cl.⁴ .......................... G01N 35/02; G01N 31/12

[52] U.S. Cl. .......................... 422/64; 422/63; 422/65; 422/68; 422/78; 422/80; 422/98; 422/102; 436/160; 177/145

[58] Field of Search .......................... 422/60, 63–68, 422/78, 79, 80, 98, 102; 177/145, 150, 152, 154; 436/160

[56] References Cited

U.S. PATENT DOCUMENTS

| | | | |
|---|---|---|---|
| 2,597,751 | 5/1952 | Ruge | 177/211 |
| 2,754,178 | 7/1956 | Mack | 436/160 |
| 3,256,948 | 6/1966 | Annen et al. | 177/211 |
| 3,684,452 | 8/1972 | Bessman | 422/64 |
| 3,790,347 | 2/1974 | Fletcher et al. | 422/78 |
| 3,826,622 | 7/1974 | Natelson | 422/65 |
| 3,843,323 | 10/1974 | Quame | 422/65 |
| 3,870,465 | 3/1975 | Marechal | 422/68 |
| 3,951,609 | 4/1976 | Palenscar | 422/64 |
| 4,039,287 | 8/1977 | Moran | 422/65 |
| 4,248,315 | 2/1981 | Falinower | 422/68 |
| 4,352,673 | 10/1982 | Espitalie et al. | 422/80 |
| 4,391,774 | 7/1983 | DuPain | 422/63 |

*Primary Examiner*—Michael S. Marcus

*Attorney, Agent, or Firm*—Vytas R. Matas; Robert J. Edwards

[57] ABSTRACT

A method and apparatus for on-line analysis of a coal sample. Four radial arms (16) extend from the output shaft (28) of an indexing motor (14). Sample cups (12) at the ends of the arms are indexed along a circular path past a filling station (18) where the cup is filled with pulverized coal, an analyzing station (20) where various chemical analyses are performed on the coal sample, a dumping station station (22) where the residue of the coal sample is dumped for disposal, and a cleaning station (24) where the sample cup is cleaned in preparation for another analysis cycle.

9 Claims, 1 Drawing Figure

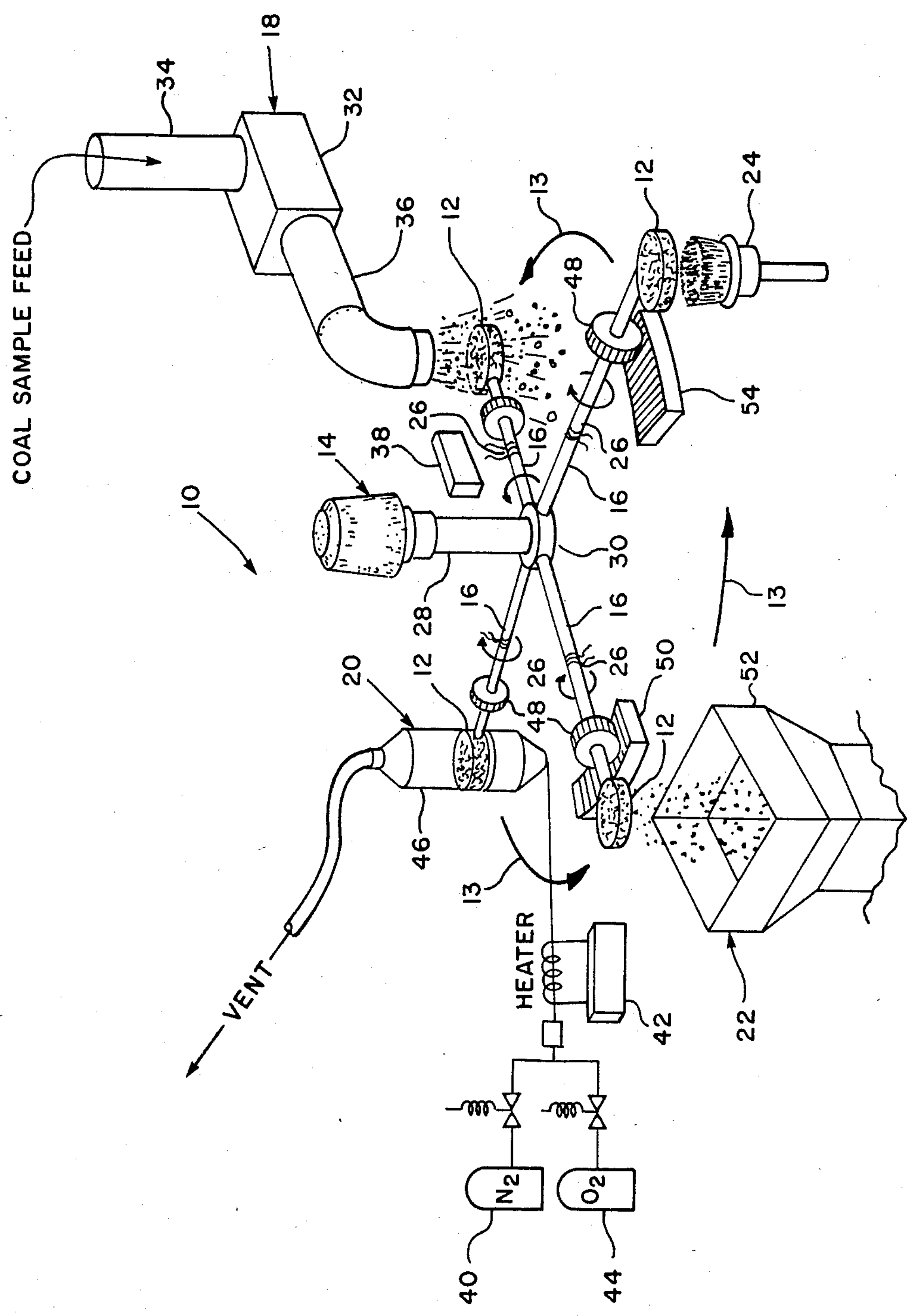
COAL SAMPLE FEED
VENT
HEATER
$N_2$
$O_2$
10
12
13
14
16
18
20
22
24
26
28
30
32
34
36
38
40
42
44
46
48
50
52
54

ON-LINE COAL ANALYZER

This application is a continuation of application Ser. No. 395,427, filed July 6, 1982, now abandoned.

TECHNICAL FIELD

The present invention relates generally to coal analyzers, and more particularly to an on-line coal analyzer wherein chemical analyses are automatically performed on coal samples.

BACKGROUND ART

Coal analysis in the facilities of large coal users is generally accomplished by traditional laboratory techniques performed on coal grab samples. Such sampling requires a plurality of manual manipulations, and the analyses are very time consumming.

Some attempts have recently been made to provide on line, real time analyses. For example, automated instruments have been developed using radiation techniques wherein an instrument straddles a coal feeder belt and irradiates the coal with neutrons or gamma radiation. Re-radiation of the elements of the coal is detected and the coal constituents are determined by computer analysis.

While such devices are effective, they are very large and expensive, and since they deal with inherently dangerous materials they are subject to extensive government licensing and safety procedures which add to the total cost of operation.

Because of the foregoing, it has become desirable to develop an on-line, radiation-free, automatic system for analyzing coal samples.

SUMMARY OF THE INVENTION

The present invention solves the aforementioned problems associated with the prior art as well as other problems by providing a method and apparatus for automatically weighing coal samples and performing chemical analyses of the samples. The apparatus provided can be very compact and relatively inexpensive to construct and maintain. Also no inherently hazardous constituents are used in the analyses.

More specifically, the invention provides a plurality of stations distributed about a central indexing motor drive. A plurality of sampling cups are attached to rotary arms attached to the motor drive. The analyzing system includes a sampling station where coal is automatically extracted from the main coal feed system, an analyzing station where all the chemical analyses are performed, a dumping station where the coal residue is dumped from the sampling cups, and a cleansing station where the sampling cups are cleaned in preparation for the next sampling cycle. There is a sampling cup for each station so that the various steps in the process are performed simultaneously as the sampling cups are indexed to each station. A strain gauge or similar device is provided on each sampling arm so that the weight of each sampling cup can be continuously monitored.

BRIEF DESCRIPTION OF THE DRAWING

The single FIGURE of the drawing is a perspective view schematically representing the apparatus of the invention.

DESCRIPTION OF THE PREFERRED EMBODIMENT

Referring now to the drawing where the illustration is for the purpose of describing the preferred embodiment of the invention and is not intended to limit the invention hereto, the FIGURE illustrates an analyzing system, designated generally by the numeral 10, which comprises a plurality of sampling cups 12, which are indexed along a circular path depicted by the arrows 13 by means of a central indexing motor drive unit 13 which drives the cups through radially extending arms or shafts 16; and a plurality of functional stations including a sampling station 18, an analyzing station 20, a dumping station 22 where the sample residue is dumped into a waste hopper, and a cleaning station 24 where each sample cup is cleaned for reuse in another analyzing cycle.

Each of the sampling cups 12 is a shallow open cylinder made from a porous metal such as sintered stainless steel, inconel, or another durable, inert material. Each of the radial arms 16 has a strain gauge 26 or other suitable device attached to it and connected to a central controller through slip rings or the like to provide accurate monitoring and recording of the weight of each sample cup during the various steps of an analyzing cycle.

In accordance with the preferred embodiment of the invention, the indexing motor drive 14 has a vertical output shaft 28 with a cylindrical head 30 attached to the lower end thereof. As illustrated herein, four radial arms 16 extend horizontally from the head 30, and a sampling cup 12 is fixed to the end of each arm. As will be described in further detail below, the arms 16 are mounted to be rotatable about their longitudinal axes within the head 30.

The sampling station 18 comprises a known type of pulverizer 32 for reducing a coal sample to a particle size suitable for chemical analysis, an inlet feed tube 34 leading from the coal feed system of the facility, and an outlet tube 36 adapted to direct a pulverized coal sample to a waiting cup 12 which has been indexed into position beneath the outlet tube 36. The coal sample can be extracted from the coal feed system continuously by means of an auger or other such known device.

At the sampling station the cup 12 is intentionally overfilled with the excess being returned to the main feed system. Once the cup is filled the indexing unit 14 is energized to rotate the cup 12 toward the analyzing station 20. To insure that a uniform sample is collected a stationary scraper 38 is mounted between the sampling and analyzing stations and is positioned to scrape off the excess sample even with the top of the cup to obtain a known sample volume. Since the volume of the cup is known and the weight of the sample can be determined by means of the strain gauge 26 on the arm 16, the bulk density of the sample can be calculated, for example by means of a microprocessor, in accordance with the equation:

$$\text{bulk density} = \frac{\text{total weight} - \text{tare weight}}{\text{volume}}$$

At the analyzing station 20 the sample is first dried by passing nitrogen or other inert gas from a source 40 through a heater 42, and then through the porous sample cup 12. During the drying operation the weight is monitored and the drying operation is stopped when no further significant weight loss is detected. The moisture content is then calculated by a microprocessor in accordance with the equation:

$$\text{Percent Moisture} = \frac{100 \times \text{initial sample weight} - \text{final sample weight}}{\text{initial sample weight}}$$

It is understood that during the above drying process the nitrogen temperature is controlled to prevent chemical decomposition of the coal.

After drying, the sample is pyrolized by passing oxygen from a source 44 through the heater 42 and then through the sample.

Analyses of the carbon monoxide, carbon dioxide, sulfur dioxide and nitrogen oxides are also performed at the analyzing station 20. Oxygen content is analyzed and used to control the incoming flow rate. Analyses of carbon monoxide, sulfur and nitrogen oxides can be performed using catalytic sensors placed in a vent hood 46 disposed over the sample at the analyzing station. Oxygen is measured with a known zirconia-based sensor. Electro-chemical carbon dioxide sensors can also be employed.

Other known analytical methods can also be used, for example infrared spectroscopy for carbon monoxide and carbon dioxide, and ultraviolet and visible spectroscopy for sulfur and nitrogen oxides.

Constituent concentrations are totalized during pyrolysis. The process is complete when sample weight has stabilized. Knowing the total volume of oxygen added, a material balance can be run and the total concentration of each constituent in the sample calculated. The remaining sample weight is the ash content of the sample.

Using the temperature rise information and the total volume of oxygen added, a heat balance can be run to yield the calorific content of the coal sample.

After the analyses are completed the indexing motor is energized to rotate the sample cup 12 to the dumping station 22. To permit the cup to be inverted over the dumping station, a gear 48 is mounted on each arm 16, and a rack 50 is located adjacent the station. As the arm approaches the station 22, the gear contacts the rack and rotates 180° when the cup reaches a waste hopper 52 to dump the residue.

The sample cup is then indexed to the cleaning station 24 where mechanical, ultrasonic, and/or chemical means are used to clean the cup until its tare weight returns to within a predetermined range. Adjacent the cleaning station a second rack 54 is located to rotate the cup to its normal, upright position for refilling at the sampling station in preparation for a new analysis cycle.

In the illustrated embodiment all analytical steps are indicated as being performed at a single analyzing station 20, however, it can be appreciated that additional analyzing stations can be provided to analyze other constituents and properties of the coal sample.

Certain modifications and improvements will occur to those skilled in the art upon reading the foregoing. It should be understood that all such modifications and improvements have been deleted herein for the sake of conciseness and readability, but are properly within the scope of the following claims.

I claim:

1. Apparatus for the on-line analysis of a coal sample comprising a porous sample cup of predetermined volume, a first station including means for filling said sample cup with a sample of pulverized coal, a second station including means for performing one or more analysis procedures on said sample, a third station including means for receiving the residue of said sample after completion of said analysis procedures, a fourth station including means for cleaning said sample cup, and means for indexing said sample cup sequentially from said first through said fourth stations and back to said first station, said first, second, third and fourth stations are arranged along a circular path; said indexing means comprises an indexing motor disposed centrally of said circular path, an arm extending radially from an output shaft of said indexing motor, and means attaching said sampling cup to said arm in position to traverse said circular path and means on said arm for providing a continuous indication of the weight of said sampling cup.

2. The apparatus as defined in claim 1 in which said means for filling said sampling cup is operable to overfill said sampling cup, and said sampling cup comprises a cylinder open at one end, said apparatus further including scraper means disposed along said circular path in position to scrape off the overfilled portion of said sample level with the open end of said sampling cup.

3. The apparatus as defined in claim 1 in which said porous sampling cup allows one or more gases to be passed through said cup and into the sample therein in the second station to provide for the analysis procedures therein.

4. The apparatus as defined in claim 1 including a plurality of arms extending radially from the output shaft of said indexing motor, each of said arms having a sampling cup fixed thereto, said arms being arranged to simultaneously position a sampling cup at each of said stations.

5. The apparatus as defined in claim 1 in which said arm is rotatable about its longitudinal axis, said apparatus further including means adjacent said third and fourth stations operable to engage said arm to rotate said arm as said sampling cup traverses said circular path.

6. The apparatus as defined in claim 5 including a gear fixed to said arm for rotation therewith, and said means operable to rotate said arm comprise racks arranged in position along said circular path to engage said gear.

7. Apparatus for the on-line analysis of a coal sample comprising a centrally disposed indexing motor with a rotatable shaft, a plurality of arms connected to said shaft at one end and extending radially outwardly to a free end, a heat resistant sample cup of predetermined volume being connected to said free end of each arm, each of said arms having means connected thereto for providing a continuous indication of the weight of said sampling cup, a first station means for filling said sample cup with a sample of pulverized coal, a second station including means for pyrolizing said sample while in each of said cups and performing one or more analysis procedures on said sample, a third station means for receiving the residue of said sample after completion of analysis procedures, a fourth station means for cleaning said sample cup, said stations being located along a predetermined path situated about said indexing motor and means for indexing each of said sample cups sequentially from said first through said fourth stations and back to said first stations.

8. Apparatus arranged along a circular path for the on-line analysis of a coal sample sequentially moved along stations of the circular path comprising a porous sample cup of predetermined volume, arm support means having automated weighing means for supporting said porous sample cup, a first station including means for filling said sample cup with a sample of pulverized coal, a second station including means for performing one or more analysis procedures on said sample, a third station including means for receiving the residue of said sample after completion of said analysis procedures, a fourth station including means for cleaning said sample cup means for indexing said sample cup sequentially from said first through said fourth stations and back to said first station, said second station having an upper and lower section for engaging and enclosing said sample cup and means for supplying an oxidizing gas upwardly through the lower section of the combustion chamber of said second station and upwardly through said sample cup.

9. Apparatus for on-line analysis of coal sample comprising a porous sample cup of predetermined volume, arm support means having automated weighing means for supporting said porous sample cup, a first station having means for filling said sample cup with a sample of pulverized coal of a predetermined volume and a known weight, a second station incuding insitu means for drying, pyrolyzing with heated oxygen and analyzing the sample using electrochemical analyzers, a third station including means for dumping the sample after the completion of the drying and analyzing procedures by rotating the sample cup 180°, a fourth station having means for cleaning the sample cup and means for moving the sample cup from said first through said fourth station along a circular configuration.

* * * * *

UNITED STATES PATENT AND TRADEMARK OFFICE
CERTIFICATE OF CORRECTION

PATENT NO. : 4,562,044

DATED : 12/31/85

INVENTOR(S) : Thomas L. Bohl

It is certified that error appears in the above-identified patent and that said Letters Patent are hereby corrected as shown below:

Column 2, line 11, change "13" to --14--.

Column 3, lines 5, change the formula to read as follows:

$$\text{percent moisture} = 100 \times \frac{\text{initial sample weight} - \text{final sample weight}}{\text{initial sample weight}}$$

Signed and Sealed this

Sixth Day of January, 1987

*Attest:*

DONALD J. QUIGG

*Attesting Officer*

*Commissioner of Patents and Trademarks*